(12) United States Patent
Sheskey et al.

(10) Patent No.: US 8,685,373 B2
(45) Date of Patent: Apr. 1, 2014

(54) MUCOSAL OR CUTANEOUS MEDICINAL OR HYGIENE SYSTEM

(75) Inventors: Paul J. Sheskey, Midland, MI (US); Colin M. Keary, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 1700 days.

(21) Appl. No.: 11/660,664

(22) PCT Filed: Aug. 25, 2005

(86) PCT No.: PCT/US2005/030493
§ 371 (c)(1),
(2), (4) Date: Feb. 20, 2007

(87) PCT Pub. No.: WO2006/036417
PCT Pub. Date: Apr. 6, 2006

(65) Prior Publication Data
US 2007/0243141 A1    Oct. 18, 2007

Related U.S. Application Data

(60) Provisional application No. 60/612,627, filed on Sep. 23, 2004.

(51) Int. Cl.
*A61K 9/12* (2006.01)
*A61K 9/00* (2006.01)
*A01N 25/02* (2006.01)

(52) U.S. Cl.
USPC ............................. 424/44; 424/400; 424/43

(58) Field of Classification Search
USPC .......................................... 424/400, 44, 43
See application file for complete search history.

(56) References Cited

U.S. PATENT DOCUMENTS

| 4,565,647 | A | * | 1/1986 | Llenado ........................... 516/14 |
| 4,683,004 | A | | 7/1987 | Goddard |
| 5,048,750 | A | | 9/1991 | Tobler |
| 5,369,131 | A | | 11/1994 | Poli et al. |
| 5,750,585 | A | * | 5/1998 | Park et al. ....................... 521/143 |
| 6,010,716 | A | | 1/2000 | Saunal et al. |
| 6,086,856 | A | | 7/2000 | Saferstein et al. |
| 6,544,539 | B1 | * | 4/2003 | Ricketts ........................ 424/405 |
| 7,011,702 | B2 | * | 3/2006 | Sheskey et al. ................ 106/122 |
| 2004/0151756 | A1 | | 8/2004 | Richards et al. |
| 2004/0265240 | A1 | | 12/2004 | Tamarkin et al. |

FOREIGN PATENT DOCUMENTS

| EP | 0 362 655 | 4/1990 |
| EP | 0 510 561 | 7/1996 |
| EP | 1 120 109 | 8/2001 |
| EP | 1 210 935 | 6/2002 |
| JP | 10-087456 | 4/1998 |
| JP | 10-114636 | 5/1998 |
| JP | 10-114637 | 5/1998 |
| WO | 96/17595 | 6/1996 |
| WO | 00/19979 | 4/2000 |
| WO | 03/020207 | 3/2003 |
| WO | WO 03/020207 | 3/2003 |

* cited by examiner

Primary Examiner — Abigail Fisher

(57) ABSTRACT

A mucosal or cutaneous medicinal or hygiene system, comprising (a) a gas-driven foam dispenser; and (b) a fluid composition comprising (i) as the only foaming agent one or more polysaccharides, gelatins, synthetic polymers selected from the group consisting of ethylene oxide homo- and copolymers having a weight average molecular weight of at least 10,000, and homo and copolymers comprising in polymerized form acrylic acid, an acrylic acid salt, acrylamide, vinylalcohol, vinylacetate, vinylpyrrolidone or vinylpyridine, or a combination thereof; (ii) a liquid diluent, and (iii) an active ingredient for mucosal or cutaneous medicinal treatment or hygiene.

8 Claims, No Drawings

MUCOSAL OR CUTANEOUS MEDICINAL OR HYGIENE SYSTEM

CROSS REFERENCE TO RELATED APPLICATIONS

This application is a 371 of PCT/US2005/030493 filed Aug. 25, 2005, which claims the benefit of U.S. Provisional Application Ser. No. 60/612,627 filed Sep. 23, 2004.

The present invention relates to a system for delivering a mucosal or cutaneous medicinal or hygiene composition in the form of a foam.

BACKGROUND OF THE INVENTION

Oral medicinal or oral hygiene products exist in a wide variety of forms, such as tablets, capsules, liquids or sprays. When applying the oral medicinal or oral hygiene products in the form of a liquid, typically a measured quantity of the product is applied to the oral cavity by means of a spoon. Unfortunately, such liquids are frequently spilled, especially when they are applied to children or elderly people. Spilling can lead to inaccuracies of the applied dosage. Therefore, much research has been spent on developing new ways of applying liquid oral medicinal or oral hygiene products.

European Patent Application 1,210,935 A1 discloses an oral medicinal composition which comprises an active ingredient and at least one foaming agent, which is ejected from a foam-developing device. The medicinal composition is said to be useful for aged persons, children or patients with swallowing difficulties. A variety of monomeric and polymeric low molecular weight compounds are listed as foaming agents, preferably a mixture of polyethylene glycol and polysorbate or a mixture of polyethylene glycol and sodium lauryl sulfate. When polyethylene glycol is used as a foaming agent, for example polyethylene glycol of a molecular weight of 6000, the duration of the resulting self-sustainable foam is short. When sodium lauryl sulfate or a polysorbate, such as polysorbate 80 with a molecular weight of about 1300, is used as a foaming agent, the duration of the resulting self-sustainable foam is long. EP 1,210,935 A1 teaches that the resulting self-sustainable foam is influenced by the mean molecular weight of the foaming agent. It suggests to prepare a combination of plural foaming agents by utilizing such properties and further modifying the blend ratios or blend quantities to adjust the duration of the resulting self-sustainable foam depending on the applicable drug or the subject patient. It also teaches that the medicinal composition with a longer duration of self-sustainable foam can be achieved by adding an appropriate viscous agent other than a foaming agent. Various polymeric compounds are listed as viscous agents, such as propylene glycol alginate, various cellulose ethers, starches, polyvinylpyrrolidone, or yellow beeswax. However, variation of the duration of the resulting self-sustainable foam by blending a plurality of foaming agents and in some cases a viscous agent in addition to the plurality of foaming agents is inconvenient. Also, the more different types of foaming agents and thickeners are incorporated into an oral medicinal composition, the higher is the risk of incompatibilities.

U.S. Pat. No. 6,086,856 discloses oral hygiene formulations which comprise foaming surfactants. They are dispensed in the form of foams by means of an air-driven propellant-less dispenser. The formulation comprises an oral surfactant, a compound effective for oral hygiene and water containing up to 25 weight percent of ethanol. An anionic surfactant is used, such as sodium lauryl sulfate, alone or in combination with nonionic surfactants, such as poly(oxyethylene)—poly(oxypropylene) block copolymers.

Unfortunately, sodium lauryl sulfate that is recommended in both above-mentioned patent publications as a preferred foaming agent is a moderately toxic material (Handbook of Pharmaceutical Excipients, Fourth Edition, page 569).

U.S. Pat. No. 5,369,131 discloses oral, cutaneous and intravaginal pharmaceutical compositions which can be administered as a foam by means of a propellant free delivery device. The pharmaceutical composition comprises a surfactant, a solvent, an active ingredient and optionally a mucoadhesive polymer. Alkylamidobetaine, quarternary ammonium salts, poloxamers (polyoxyethylene-polyoxypropylene) copolymers and phospholipids are disclosed as surfactants. Unfortunately, the use of these surfactants limits the types of active ingredients that are compatible with these surfactants and that can be included in the pharmaceutical composition.

In view of the many different specific applications of foamable medicinal or hygiene systems, it is evident that the few known systems cannot satisfy all needs. Accordingly, one object of the present invention is to provide another system for delivering a mucosal or cutaneous medicinal or hygiene composition in the form of a foam. A preferred object of the present invention is to provide a system for delivering a mucosal or cutaneous medicinal or hygiene composition in the form of a foam which can be administered with a spoon without spilling even if the spoon is not kept in horizontal position. It is another preferred object of the present invention to provide such system which is capable of delivering a self-sustainable foam of which the duration can be controlled and if desirable varied without the need of mixing a plurality of foaming agents.

SUMMARY OF THE INVENTION

One aspect of the present invention is a mucosal or cutaneous medicinal or hygiene system, comprising
(a) a gas-driven foam dispenser; and
(b) a fluid composition comprising
   (i) as the only foaming agent one or more polysaccharides, gelatins, synthetic polymers selected from the group consisting of ethylene oxide homo- and copolymers having a weight average molecular weight of at least 10,000, and homo- and copolymers comprising in polymerized form acrylic acid, an acrylic acid salt, acrylamide, vinylalcohol, vinylacetate, vinylpyrrolidone or vinylpyridine, or a combination thereof;
   (ii) a liquid diluent, and
   (iii) an active ingredient for mucosal or cutaneous medicinal treatment or hygiene.

Another aspect of the present invention is a kit for delivering a mucosal or cutaneous medicinal or hygiene system wherein the kit comprises (a) a gas-driven foam dispenser and (b) a separately packed volume of an above-described fluid composition.

DETAILED DESCRIPTION OF THE INVENTION

The term "mucosal or cutaneous medicinal or hygiene system" includes, but is not limited to, systems which are intended for oral medicinal or hygiene treatment, for medicinal or hygiene treatment of the skin, and for otic, nasal, genital, vaginal or anal medicinal treatment. Systems for oral medicinal or hygiene treatment are preferred and include those which are intended to be ingested, such as a pharmaceutical compositions, but also buccal systems which are intended for application to the oral cavity, such as pharmaceutical compositions for treating the oral cavity or oral hygiene products like gargles, mouthwashes or tooth cleaning formulations.

The fluid composition comprises as the only foaming agent one or more polysaccharides, one or more gelatins, one or more synthetic polymers selected from the group consisting of ethylene oxide homo- and copolymers having a weight average molecular weight of at least 10,000, and homo- and copolymers comprising in polymerized form acrylic acid, an acrylic acid salt, acrylamide, vinylalcohol, vinylacetate, vinylpyrrolidone or vinylpyridine, or a combination of one or more polysaccarides, one or more gelatins and/or one or more of said synthetic polymers. Water-soluble polymers are preferred.

Examples of polysaccharides include gum arabic, xanthan gum, gum karaya, gum tragacanth, gum ghatti, carrageenan, dextran, alginates, agar, gellan gum, gallactomannans such as guar gum, pectins, starches, starch derivatives, guar derivatives and xanthan derivatives. Starch derivatives, guar derivatives and xanthan derivatives are described in more detail in European patent EP 0 504 870 B, page 3, lines 25-56 and page 4, lines 1-30. Useful starch derivatives are for example starch ethers, such as hydroxypropyl starch or carboxymethyl starch. Useful guar derivatives are for example carboxymethyl guar, hydroxypropyl guar, carboxymethyl hydroxypropyl guar or cationized guar. Preferred hydroxypropyl guars and the production thereof is described in U.S. Pat. No. 4,645,812, columns 4-6. Preferred polysaccharides are cellulose esters or cellulose ethers. Preferred cellulose ethers are carboxy-$C_1$-$C_3$-alkyl celluloses, such as carboxymethyl celluloses; carboxy-$C_1$-$C_3$-alkyl hydroxy-$C_1$-$C_3$-alkyl celluloses, such as carboxymethyl hydroxyethyl celluloses; $C_1$-$C_3$-alkyl celluloses, such as methylcelluloses; $C_1$-$C_3$-alkyl hydroxy-$C_{1-3}$-alkyl celluloses, such as hydroxyethyl methylcelluloses, hydroxypropyl methylcelluloses or ethyl hydroxyethyl celluloses; hydroxy-$C_{1-3}$-alkyl celluloses, such as hydroxyethyl celluloses or hydroxypropyl celluloses; mixed hydroxy-$C_1$-$C_3$-alkyl celluloses, such as hydroxyethyl hydroxypropyl celluloses, or alkoxy hydroxyethyl hydroxypropyl celluloses, the alkoxy group being straight-chain or branched and containing 2 to 8 carbon atoms. Most preferably, the fluid composition comprises a water-soluble cellulose ether, such as a methylcellulose with a methyl molar substitution $DS_{methoxyl}$ of from 0.5 to 3.0, preferably from 1 to 2.5, or a hydroxypropyl methylcellulose with a $DS_{methoxyl}$ of from 0.5 to 3.0, preferably from 1 to 2.5 and a $MS_{hydroxypropoxyl}$ of from 0.05 to 2.0, preferably from 0.1 to 1.5.

The polysaccharides and the above-mentioned synthetic polymers generally have a weight average molecular weight of at least 10,000, preferably at least 12,000, more preferably at least 15,000. The preferred upper limit for the weight average molecular weight largely depends on the type of polymer. Generally the weight average molecular weight of the polymer i) is up to 1,000,000, preferably up to 500,000, more preferably up to 100,000. Most preferably, the polysaccharides and the above-mentioned synthetic polymers have a weight average molecular weight of from 12,000 to 100,000.

The polysaccharides and the above-mentioned synthetic polymers are the only foaming agent. This means that the fluid composition does not contain a known monomeric surfactant, such as sodium lauryl sulfate, or a low-molecular weight polymeric surfactant with a weight average molecular weight of less than 8,000, particularly less 10,000, such as a polyethylene glycol or polysorbate, in a sufficient amount to contribute to the foaming of the fluid composition upon contact with air. More preferably, the fluid composition does not comprise any detectable amount of such a surfactant.

The fluid composition preferably comprises from 0.001 to 10 percent, more preferably from 0.01 to 8 percent, most preferably from 0.1 to 5 percent of the above-mentioned foaming agent, based on the total weight of the fluid composition. It has been found that by controlling and, if desirable, varying the molecular weight of an above-mentioned foaming agent, preferably a cellulose ether, or its concentration in the fluid composition or both, the fluid composition is capable of delivering a self-sustainable foam of which the duration can be controlled and, if desirable, varied. The mentioned polymers are available at various molecular weights. Furthermore, solutions of various concentrations can be prepared. Although the fluid composition may comprise two or more of the above-mentioned foaming agents, the duration of the self-sustainable foam can be controlled and/or varied without the need of mixing a plurality of foaming agents. It is a substantial advantage of the present invention that a tailor-made foam can be provided depending on the intended end-use. Most preferably, the fluid composition comprises one single foaming agent. Even when using a single foaming agent, according to the present invention foams can be produced which collapse fast but also foams can be produced which are long-lasting by selecting the molecular weight and concentration of the foaming agent according to the teaching provided herein. The concentration and the molecular weight of the foaming agent is generally chosen such that the viscosity of the fluid composition is from 0.1 to 500, preferably from 0.5 to 400, more preferably from 1 to 200 mPa·s, most preferably from 2 to 50 mPa·s at 20° C. The viscosities can be measured using a rotational viscometer. It has been found that fluid compositions of a viscosity from 2 to 50 mPa·s at 20° C. provide foams with optimum spilling resistance when administered by a spoon or a similar device. However, it is to be understood that the present invention is not limited to systems for producing foams which are administered by a spoon. Alternatively, the foam can be directly administered from the dispenser to the human being or animal. The foam can readily be applied to a cavity or to a surface of an individual or animal to be treated where the foam gradually resumes the initial liquid form.

The fluid composition further comprises a liquid diluent. The term "liquid diluent" means a diluent that is liquid at normal pressure and 25° C. The liquid diluent preferably is a monomeric compound or an oligomeric compound with a molecular weight of up to 500, preferably up to 300. Useful organic liquids are alcohols, preferably monofunctional alcohols, such as ethanol, or oils, such as paraffin oils, animal oils or vegetable oils. The liquid diluent is preferably water-based. This means that the water content is preferably more than 50 percent, more preferably at least 80 percent, based on the total weight of the liquid diluent in the composition. The most preferred liquid diluent is water or a water-ethanol mixture.

The fluid composition further comprises an active ingredient for mucosal or cutaneous medicinal treatment or hygiene.

A preferred embodiment of the present invention is an oral medicinal system intended for use by human beings or animals. Preferred active ingredients for oral delivery of a medicinal treatment are acetaminophen (Tylenol™ and generics), ibuprofen (Advil™, Motrin™), vitamins, herbals and mineral supplements (Centrum™ and generics), naproxen sodium (Aleve™), antacids, diphenhydrainine HCl (Benadryl™ and generics); cough, cold, allergy, and sinus medications, anti-diarrheals (Imodium™); chlorpheniramine maleate; cimetidine; dextromethorphan HBr; and simethicone.

Another preferred embodiment of the present invention is an oral hygiene system intended for use by human beings.

Active ingredients for oral hygiene are for example oral antimicrobial (including antibacterial, antifungal and antiseptic) agents, anti-plaque agents, and anti-carious agents. Useful active ingredients for oral hygiene are disclosed in U.S. Pat. No. 6,086,856, column 6, lines 14-67 and column 7, lines 1-9.

Another preferred embodiment of the present invention is a cutaneous medicinal or hygiene system for use in the veterinary science. Applying a topical fluid composition in the form of a foam is particularly useful for treating animals. When applying a liquid medicinal or hygiene system, spreading the liquid on the surface of the animal is necessary to prevent that the system drips off quickly. Depending on the animal this can be very difficult or even dangerous. By applying a foam this disadvantage can be prevented. Active ingredients useful in the veterinary science for treating animals are known in the art.

The concentration of an active ingredient largely depends on the end-use and the specific type of active ingredient. Typically their concentration is from 0.005 to 5 percent, based on the total weight of the fluid composition.

The fluid composition may comprise one or more additional solid or liquid components such as fillers, pigments, colors, dyes, fragrances or flavors. If present, their total amount is generally up to 10 percent, preferably up to 5 percent, more preferably up to 2.5 percent, based on the total weight of the fluid composition. Although the fluid composition may comprise a propellant, the inclusion of a propellant is usually neither necessary nor desirable. Preferably, the fluid composition is propellant-less.

The mucosal or cutaneous medicinal or hygiene system comprises the above-described fluid composition in a gas-driven foam dispenser. Preferred gases are oxygen, nitrogen, carbon dioxide or, more preferably, air. Air-driven foam dispensers are preferred and known in the art. For example, they are described in U.S. Pat. No. 5,048,750. A variety of air-driven foam dispensers are commercially available from Airspray N.V. in the Netherlands or from Airspray International Inc. in the USA. The dispenser is preferably a pump container. The air within the container can be brought into a state of increased pressure on demand by simply compressing it, thereby providing a sufficient driving force to produce and dispense foam from the device. The dispenser is also designed to have the air supply automatically replenished by allowing the container to decompress. Advantageously, the foam dispenser is only air driven and functions in the absence of a propellant. The dispenser may be multi-chambered to allow the use of incompatible or reactive ingredients; in such a device the ingredients only come into contact with each other upon ejection from the dispenser as a foam. The fluid composition is contacted with the gas in the foam dispenser to foam the composition and to eject the foamed composition from the dispenser.

The foam produced in the gas-driven, preferably air-driven foam dispenser comprises a discontinuous gas phase and a continuous fluid phase, preferably an aqueous phase, comprising the foaming agent, the active ingredient, optional additives and bound liquid. Generally the lamella or fluid film of the gas bubbles is viscous due to the presence of the chosen foaming agent. Water is retained in the lamella of the gas bubbles. The drainage of the liquid from the lamellae is minimized, reduced or prevented; such a foam is designated as "non-draining foam" in the art. It has been found that surprisingly high foam qualities can be achieved. Generally the achieved foam quality is from 52 to 95 percent, preferably from 60 to 90 percent. The foam quality FQ is given in percent at atmospheric pressure and 25° C. and is defined as follows:

$$FQ(\%) = [\text{gas volume}/(\text{gas volume} + \text{fluid volume}) \times 100].$$

The foam quality can be measured by measuring the foam volume that is produced from a given volume of fluid at atmospheric pressure and 25° C.

The foam generally has a density of 0.01 to 0.5 g/cm$^3$, typically from 0.1 to 0.5 g/cm$^3$.

EXAMPLES

The present invention is further illustrated by the following examples which should not be construed to limit the scope of the invention. All parts and percentages are by weight unless otherwise indicated. The methyl and hydroxypropyl substitutions of the cellulose ethers listed in the examples below are measured and calculated according to ASTM D3876. The apparent viscosities indicated in the examples below are measured and normalized to a .2 weight percent aqueous solution using an Ubbelohde viscometer at 20° C. The cellulose ethers listed in Table 1 are used as foaming agents in the following examples.

TABLE 1

| | |
|---|---|
| E3PLV | Hydroxypropyl methylcellulose with a methoxyl substitution of 28-30 percent, a hydroxypropoxyl substitution of 7-12 percent and a viscosity of about 3 mPa · s. It is commercially available from The Dow Chemical Company under the Trademark METHOCEL E3PLV. |
| K3PLV | Hydroxypropyl methylcellulose with a methoxyl substitution of 19-24 percent, a hydroxypropoxyl substitution of 7-12 percent and a viscosity of about 3 mPa · s. It is commercially available from The Dow Chemical Company under the Trademark METHOCEL K3PLV. |
| E6PLV | Hydroxypropyl methylcellulose with a methoxyl substitution of 28-30 percent, a hydroxypropoxyl substitution of 7-12 percent and a viscosity of about 6 mPa · s. It is commercially available from The Dow Chemical Company under the Trademark METHOCEL E6PLV. |
| A15PLV | Methylcellulose with a methoxyl substitution of 28-31 percent and a viscosity of about 15 mPa · s. It is commercially available from The Dow Chemical Company under the Trademark METHOCEL A15PLV. |
| K100PLV | Hydroxypropyl methylcellulose with a methoxyl substitution of 19-24 percent, a hydroxypropoxyl substitution of 7-12 percent and a viscosity of about 100 mPa · s. It is commercially available from The Dow Chemical Company under the Trademark METHOCEL K100PLV. |
| E4MP | Hydroxypropyl methylcellulose with a methoxyl substitution of 28-30 percent, a hydroxypropoxyl substitution of 7-12 percent and a viscosity of about 4000 mPa · s. It is commercially available from The Dow Chemical Company under the Trademark METHOCEL E4MP. |
| K4MP | Hydroxypropyl methylcellulose with a methoxyl substitution of 19-24 percent, a hydroxypropoxyl substitution of 7-12 percent and a viscosity of about 4,000 mPa · s. It is commercially available from The Dow Chemical Company under the Trademark METHOCEL K4MP. |

Various cellulose ethers are dissolved in water to provide a range of chemistries and viscosities for evaluation of the aqueous solutions in foam dispensers. Table 2 below lists the specific cellulose ethers and their concentrations in percent, based on the total weight of the aqueous solution, that are used to achieve the desired solution viscosities of 100, 50, 25 and 3 mPa·s respectively. Foams are produced from these aqueous cellulose ether solutions and tested as described in Examples 1-15.

TABLE 2

| | Percent Concentrations to achieve desired Viscosity | | | | |
|---|---|---|---|---|---|
| Viscosity mPa·s | 100.00 | 50.00 | 25.00 | 3.00 | Viscosity mPa·s |
| E3PLV | 10.57 | 8.57 | 6.73 | 2.00 | E3PLV |
| K3PLV | 10.57 | | | 2.00 | K3PLV |
| E6PLV | 6.20 | 5.02 | 3.95 | 1.17 | E6PLV |
| A15PLV | 3.86 | 3.13 | 2.46 | 0.73 | A15PLV |
| K100PLV | 2.00 | 1.62 | 1.27 | 0.38 | K100PLV |
| E4MP | 0.86 | 0.69 | 0.54 | 0.16 | E4MP |
| K4MP | 0.86 | | | 0.16 | K4MP |

Example 1

An aqueous K4MP solution of a concentration of 0.16 or 0.86 percent is filled into an air-driven foam dispenser which is made of high density polyethylene, has a volume of 250 ml and is commercially available from Airspray N.V. International Inc. under the designation Table Top 250 ml HDPE. To determine variation in density of dispensed foam and how it is affected by the viscosity of the solution, a standard container of 55.36 cm³ volume is filled with the foam ejected from the dispenser. Then the filled container is weighed. The foam density is calculated by dividing the weight of the foam by the volume of the container. The foam quality is calculated according to the formula disclosed further above. The experiment is repeated eight times. The results are given in Table 3.

TABLE 3

| 0.16% K4MP | | | 0.86% K4MP | | |
|---|---|---|---|---|---|
| Weight (g) | Density (g·cm⁻³) | Quality | Weight (g) | Density (g·cm⁻³) | Quality |
| 10.68 | 0.19 | 81% | 19.41 | 0.35 | 65% |
| 10.76 | 0.19 | 81% | 18.42 | 0.33 | 67% |
| 10.66 | 0.19 | 81% | 18.68 | 0.34 | 66% |
| 11.06 | 0.20 | 80% | 18.91 | 0.34 | 66% |
| 11.18 | 0.20 | 80% | 18.27 | 0.33 | 67% |
| 10.65 | 0.19 | 81% | 17.35 | 0.31 | 69% |
| 10.77 | 0.19 | 81% | 18.45 | 0.33 | 67% |
| 11.14 | 0.20 | 80% | 17.24 | 0.31 | 69% |
| average density: 0.20 | average quality: 80% | | average density: 0.33 | average quality: 67% | |

Example 2

Example 1 is repeated, except that aqueous E4MP solutions of a concentration of 0.16, 0.54, 0.69, and 0.86 percent are filled into foam dispensers. The results are given in Table 4.

Example 3

Example 1 is repeated, except that aqueous K100PLV solutions of a concentration of 0.38, 1.27, 1.62, and 2.0 percent are filled into foam dispensers. The results are given in Table 5.

Example 4

Example 1 is repeated, except that aqueous A15PLV solutions of a concentration of 0.73, 2.46, 3.13, and 3.86 percent are filled into foam dispensers. The results are given in Table 6.

Example 5

Example 1 is repeated, except that aqueous E6PLV solutions of a concentration of 1.17, 3.95, 5.02, and 6.20 percent are filled into foam dispensers. The results are given in Table 7.

TABLE 4

| 0.16% E4MP | | | 0.54% E4MP | | | 0.69% E4MP | | | 0.86% E4MP | | |
|---|---|---|---|---|---|---|---|---|---|---|---|
| Weight (g) | Density (g·cm⁻³) | Quality | Weight (g) | Density (g·cm⁻³) | Quality | Weight (g) | Density (g·cm⁻³) | Quality | Weight (g) | Density (g·cm⁻³) | Quality |
| 9.24 | 0.17 | 83% | 13.36 | 0.24 | 76% | 14.70 | 0.27 | 73% | 16.15 | 0.29 | 71% |
| 9.08 | 0.16 | 84% | 13.04 | 0.24 | 76% | 14.15 | 0.26 | 74% | 16.24 | 0.29 | 71% |
| 9.17 | 0.17 | 83% | 12.52 | 0.23 | 77% | 13.78 | 0.25 | 75% | 16.01 | 0.29 | 71% |
| 9.66 | 0.17 | 83% | 13.03 | 0.24 | 76% | 14.22 | 0.26 | 74% | 16.69 | 0.30 | 70% |
| 9.57 | 0.17 | 83% | 12.93 | 0.23 | 77% | 14.04 | 0.25 | 75% | 16.64 | 0.30 | 70% |
| 9.39 | 0.17 | 83% | 12.08 | 0.22 | 78% | 14.60 | 0.26 | 74% | 16.62 | 0.30 | 70% |
| 9.42 | 0.17 | 83% | 12.64 | 0.23 | 77% | 14.51 | 0.26 | 74% | 16.04 | 0.29 | 71% |
| 9.73 | 0.18 | 82% | 12.74 | 0.23 | 77% | 13.80 | 0.25 | 75% | 16.79 | 0.30 | 70% |
| average density: 0.17 | average quality: 83% | | average density: 0.23 | average quality: 77% | | average density: 0.26 | average quality: 74% | | average density: 0.30 | average quality: 70% | |

TABLE 5

| 0.38% K100PLV | | | 1.27% K100PLV | | | 1.62% K100PLV | | | 2% K100PLV | | |
|---|---|---|---|---|---|---|---|---|---|---|---|
| Weight (g) | Density (g·cm$^{-3}$) | Quality | Weight (g) | Density (g·cm$^{-3}$) | Quality | Weight (g) | Density (g·cm$^{-3}$) | Quality | Weight (g) | Density (g·cm$^{-3}$) | Quality |
| 7.10 | 0.13 | 87% | 12.59 | 0.23 | 77% | 16.31 | 0.29 | 71% | 19.77 | 0.36 | 64% |
| 7.30 | 0.13 | 87% | 14.58 | 0.26 | 74% | 17.66 | 0.32 | 68% | 21.58 | 0.39 | 61% |
| 7.10 | 0.13 | 87% | 15.84 | 0.29 | 71% | 16.87 | 0.30 | 70% | 20.53 | 0.37 | 63% |
| 7.04 | 0.13 | 87% | 15.64 | 0.28 | 72% | 16.72 | 0.30 | 70% | 20.44 | 0.37 | 63% |
| 7.56 | 0.14 | 86% | 13.38 | 0.24 | 76% | 17.44 | 0.32 | 68% | 21.20 | 0.38 | 62% |
| 7.02 | 0.13 | 87% | 12.71 | 0.23 | 77% | 17.29 | 0.31 | 69% | 20.89 | 0.38 | 62% |
| 6.90 | 0.12 | 88% | 13.31 | 0.24 | 76% | 17.76 | 0.32 | 68% | 20.86 | 0.38 | 62% |
| 6.90 | 0.12 | 88% | 12.20 | 0.22 | 78% | 17.92 | 0.32 | 68% | 20.85 | 0.38 | 62% |
| | average density: 0.13 | average quality: 87% | | average density: 0.25 | average quality: 75% | | average density: 0.31 | average quality: 69% | | average density: 0.38 | average quality: 62% |

TABLE 6

| 0.73% A15PLV | | | 2.46% A15PLV | | | 3.13% A15PLV | | | 3.86% A15PLV | | |
|---|---|---|---|---|---|---|---|---|---|---|---|
| Weight (g) | Density (g·cm$^{-3}$) | Quality | Weight (g) | Density (g·cm$^{-3}$) | Quality | Weight (g) | Density (g·cm$^{-3}$) | Quality | Weight (g) | Density (g·cm$^{-3}$) | Quality |
| 6.81 | 0.12 | 88% | 8.71 | 0.16 | 84% | 16.36 | 0.30 | 70% | 24.31 | 0.44 | 56% |
| 7.20 | 0.13 | 87% | 8.87 | 0.16 | 84% | 15.45 | 0.28 | 72% | 24.81 | 0.45 | 55% |
| 7.16 | 0.13 | 87% | 8.84 | 0.16 | 84% | 16.17 | 0.29 | 71% | 25.44 | 0.46 | 54% |
| 7.00 | 0.13 | 87% | 8.71 | 0.16 | 84% | 15.13 | 0.27 | 73% | 25.03 | 0.45 | 55% |
| 7.21 | 0.13 | 87% | 8.87 | 0.16 | 84% | 15.62 | 0.28 | 72% | 24.94 | 0.45 | 55% |
| 7.09 | 0.13 | 87% | 8.82 | 0.16 | 84% | 15.20 | 0.27 | 73% | 24.34 | 0.44 | 56% |
| 7.19 | 0.13 | 87% | 8.79 | 0.16 | 84% | 15.73 | 0.28 | 72% | 24.78 | 0.45 | 55% |
| 7.24 | 0.13 | 87% | 8.80 | 0.16 | 84% | 15.25 | 0.28 | 72% | 24.62 | 0.44 | 56% |
| | average density: 0.13 | average quality: 87% | | average density: 0.16 | average quality: 84% | | average density: 0.28 | average quality: 72% | | average density: 0.45 | average quality: 55% |

TABLE 7

| 1.17% E6PLV | | | 3.95% E6PLV | | | 5.02% E6PLV | | | 6.20% E6PLV | | |
|---|---|---|---|---|---|---|---|---|---|---|---|
| Weight (g) | Density (g·cm$^{-3}$) | Quality | Weight (g) | Density (g·cm$^{-3}$) | Quality | Weight (g) | Density (g·cm$^{-3}$) | Quality | Weight (g) | Density (g·cm$^{-3}$) | Quality |
| 6.59 | 0.12 | 88% | 6.90 | 0.12 | 88% | 8.34 | 0.15 | 85% | 13.67 | 0.25 | 75% |
| 6.48 | 0.12 | 88% | 6.92 | 0.13 | 88% | 8.35 | 0.15 | 85% | 13.50 | 0.24 | 76% |
| 6.83 | 0.12 | 88% | 6.93 | 0.13 | 87% | 8.28 | 0.15 | 85% | 13.45 | 0.24 | 76% |
| 6.74 | 0.12 | 88% | 6.82 | 0.12 | 88% | 8.42 | 0.15 | 85% | 13.55 | 0.24 | 76% |
| 6.70 | 0.12 | 88% | 6.99 | 0.13 | 87% | 8.04 | 0.15 | 85% | 13.81 | 0.25 | 75% |
| 6.56 | 0.12 | 88% | 7.16 | 0.13 | 87% | 8.04 | 0.15 | 85% | 13.51 | 0.24 | 76% |
| 6.63 | 0.12 | 88% | 7.02 | 0.13 | 87% | 8.26 | 0.15 | 85% | 13.56 | 0.24 | 76% |
| 6.72 | 0.12 | 88% | 7.13 | 0.13 | 87% | 8.17 | 0.15 | 85% | 13.21 | 0.24 | 76% |
| | average density: 0.12 | average quality: 88% | | average density: 0.13 | average quality: 87% | | average density: 0.15 | average quality: 85% | | average density: 0.24 | average quality: 76% |

Example 6

Example 1 is repeated, except that aqueous K3PLV solutions of a concentration of 2.0 and 10.57 percent are filled into foam dispensers. The results are given in Table 8.

TABLE 8

| 2.00% K3PLV | | | 10.57% K3PLV | | |
|---|---|---|---|---|---|
| Weight (g) | Density (g·cm$^{-3}$) | Quality | Weight (g) | Density (g·cm$^{-3}$) | Quality |
| 6.62 | 0.12 | 88% | 20.95 | 0.38 | 62% |
| 6.53 | 0.12 | 88% | 22.05 | 0.40 | 60% |
| 6.58 | 0.12 | 88% | 21.34 | 0.39 | 61% |
| 6.75 | 0.12 | 88% | 21.87 | 0.40 | 60% |
| 6.44 | 0.12 | 88% | 21.02 | 0.38 | 62% |
| 6.77 | 0.12 | 88% | 20.47 | 0.37 | 63% |
| 6.50 | 0.12 | 88% | 22.21 | 0.40 | 60% |
| 6.70 | 0.12 | 88% | 20.72 | 0.37 | 63% |
| | average density: 0.12 | average quality: 88% | | average density: 0.39 | average quality: 61% |

Example 7

Example 1 is repeated, except that aqueous E3PLV solutions of a concentration of 2.0, 6.73, 8.57 and 10.57 percent are filled into foam dispensers. The results are given in Table 9.

TABLE 9

| 2.00% E3PLV | | | 6.73% E3PLV | | | 8.57% E3PLV | | | 10.57% E3PLV | | |
| --- | --- | --- | --- | --- | --- | --- | --- | --- | --- | --- | --- |
| Weight (g) | Density (g·cm$^{-3}$) | Quality | Weight (g) | Density (g·cm$^{-3}$) | Quality | Weight (g) | Density (g·cm$^{-3}$) | Quality | Weight (g) | Density (g·cm$^{-3}$) | Quality |
| 6.60 | 0.12 | 88% | 7.50 | 0.14 | 86% | 9.83 | 0.18 | 82% | 19.28 | 0.35 | 65% |
| 6.74 | 0.12 | 88% | 7.64 | 0.14 | 86% | 10.18 | 0.18 | 82% | 20.35 | 0.37 | 63% |
| 6.67 | 0.12 | 88% | 7.79 | 0.14 | 86% | 10.31 | 0.19 | 81% | 21.31 | 0.38 | 62% |
| 6.81 | 0.12 | 88% | 7.62 | 0.14 | 86% | 10.20 | 0.18 | 82% | 19.14 | 0.35 | 65% |
| 6.77 | 0.12 | 88% | 7.87 | 0.14 | 86% | 10.41 | 0.19 | 81% | 19.14 | 0.35 | 65% |
| 6.64 | 0.12 | 88% | 7.48 | 0.14 | 86% | 10.87 | 0.20 | 80% | 19.06 | 0.34 | 66% |
| 6.67 | 0.12 | 88% | 7.57 | 0.14 | 86% | 10.65 | 0.19 | 81% | 18.11 | 0.33 | 67% |
| 6.59 | 0.12 | 88% | 7.66 | 0.14 | 86% | 10.30 | 0.19 | 81% | 19.43 | 0.35 | 65% |
| average density: 0.12 | | average quality: 88% | average density: 0.14 | | average quality: 86% | average density: 0.19 | | average quality: 81% | average density: 0.35 | | average quality: 65% |

Example 8

Variation in foam quantity ejected from the foam dispenser is evaluated by preparing aqueous solutions of various cellulose ethers and various concentrations and performing repeated single ejections of foam. Each ejection is weighed and results are shown in Table 10.

TABLE 10

| Cellulose ether Concentration Viscosity | E3PLV 2% 3 mPa·s Weight (g) | K4MP 0.16% 3 mPa·s Weight (g) | E3PLV 10.57% 100 mPa·s Weight (g) |
| --- | --- | --- | --- |
| | 1.51 | 1.47 | 1.70 |
| | 1.45 | 1.50 | 1.42 |
| | 1.48 | 1.47 | 1.70 |
| | 1.47 | 1.53 | 1.63 |
| | 1.48 | 1.50 | 1.66 |
| | 1.51 | 1.51 | 1.53 |
| | 1.47 | 1.47 | 1.54 |
| | 1.47 | 1.53 | 1.62 |
| | 1.48 | 1.51 | 1.65 |
| | 1.48 | 1.52 | 1.53 |
| Average | 1.48 | 1.50 | 1.60 |
| Standard Deviation | 0.0183 | 0.0238 | 0.0902 |

Example 9

To evaluate the influence of diphenhydramine hydrochloride, which is a known antihistamine, on the performance of the foam ejected from the dispenser, several solutions are prepared as shown in Table 11. The qualitative observations are also listed in Table 11. They illustrate that at least up to 50 mg/ml of the drug substance can be included in the fluid composition without significantly impacting the appearance and flow properties of the various foamed formulations.

TABLE 11

| | +2.5 mg/ml Diphenhydramine hydrochloride | +10 mg/ml Diphenhydramine hydrochloride | +25 mg/ml Diphenhydramine hydrochloride | +50 mg/ml Diphenhydramine hydrochloride |
| --- | --- | --- | --- | --- |
| 2% E3PLV | Nice foam<br>Holds shape well<br>Rather dry in apperance | Nice foam<br>Holds shape well<br>Rather dry in apperance | Nice foam<br>Holds shape well<br>Rather dry in apperance | Nice foam<br>Holds shape well/ok<br>Looks wetter in apperance than the 25 mg/ml sample.<br>Bigger bubbles in foam. |
| 2% K3PLV | Nice foam<br>Holds shape well<br>Rather dry in apperance | Nice foam<br>Holds shape well<br>Rather dry in apperance | Nice foam<br>Holds shape well<br>Looks wetter in apperance than the 10 mg/ml sample. | Wet foam<br>frothy<br>Looks wetter in apperance than the 25 mg/ml sample. |
| 0.73% A15PLV | Nice foam<br>Holds shape well<br>Rather dry in apperance | Nice foam<br>Holds shape well<br>Rather dry in apperance | Nice foam<br>Holds shape well<br>Rather dry in apperance | Nice foam<br>Holds shape well<br>Rather dry in apperance |

Example 10

To evaluate the influence of acetaminophen on the performance of the foam ejected from the dispenser, several solutions are prepared as shown in Table 12. The qualitative observations are also listed in Table 12. They illustrate that at least up to 14.28 mg/ml of the drug substance can be included in the fluid composition without significantly impacting the appearance and flow properties of the various foamed formulations.

TABLE 12

|  | +2.5 mg/ml Acetaminophen | +10 mg/ml Acetaminophen | +14.28 mg/ml Acetaminophen |
|---|---|---|---|
| 2% E3PLV | Nice foam<br>Holds shape well<br>Rather dry in apperance | Nice foam<br>Holds shape well<br>Rather dry in apperance | Nice foam<br>Holds shape well<br>Rather dry in apperance |
| 2% K3PLV | Nice foam<br>Holds shape well<br>Rather dry in apperance | Nice foam<br>Holds shape well<br>Rather dry in apperance | Nice foam<br>Holds shape well<br>Rather dry in apperance |
| 0.73% A15PLV | Nice foam<br>Holds shape well<br>Rather dry in apperance | Nice foam<br>Holds shape well<br>Rather dry in apperance | Nice foam<br>Holds shape well<br>Rather dry in apperance |

Example 11

One of the most important features of the foamed formulations is their ability to resist spilling, that means, they should not fall immediately from a spoon, or similar tool, upon inversion of the spoon. To remove variability associated with the infinite variety of spoons available, a drop test apparatus has been developed that consists of a plastic filter funnel placed into the top of a measuring cylinder of 100 ml. The measuring cylinder is equipped with motion sensors to detect a falling drop of liquid from the filter funnel into the measuring cylinder. The motion sensors stop a timer if tripped by the presence of a drop of liquid. The measuring procedure is to eject one aliquot of foam from the foam dispenser into the measuring cylinder and then to start the timer. The foam is allowed to drain or break at ambient conditions; the passage of the first drip of liquid is measured. The measured drip times provide indications of the relative stability of the various foams. Table 13 illustrates drip time results of these experiments for four foams prepared from cellulose ethers of various chemistries and two viscosities. It is apparent that the low viscosity solutions prepared from low viscosity grades of cellulose ethers give the longest drip times. The drip time can be related to the time that would be available before a foamed formulation might be expected to fall from a spoon in the extreme case that the spoon became fully inverted.

TABLE 13

| Solution Viscosity | 0.73% A15PLV 3 mPa·s | 0.16% K4MP 3 mPa·s | 2.00% E3PLV 3 mPa·s | 10.57% E3PLV 100 mPa·s |
|---|---|---|---|---|
| Drip Time (sec) | 130.91 | 1.54 | 100.24 | 1.27 |
|  | 111.21 | 1.16 | 85.56 | 0.83 |
|  | 106.01 | 1.71 | 103.44 | 0.22 |
|  | 132.42 | 2.08 | 87.73 | 0.29 |
|  | 99.63 | 1.52 | 111.14 | 0.94 |
|  | 105.71 | 0.85 | 105.91 | 0.22 |
|  | 138.90 | 1.47 | 116.96 | 0.21 |
|  | 129.11 | 1.99 | 84.35 | 0.32 |
|  | 100.29 | 1.68 | 104.05 | 0.94 |
|  | 125.89 | 2.46 | 110.07 | 0.89 |
| Average | 118.01 | 1.65 | 100.95 | 0.61 |
| Standard Deviation | 14.8665 | 0.4598 | 11.4087 | 0.3987 |

Example 12

The influence of the presence of diphenhydramine hydrochloride on the drip resistance of foams is evaluated in a series of drip-test experiments as illustrated in Table 14.

TABLE 14

|  | +2.5 mg/ml Diphenhydramine hydrochloride | +10 mg/ml Diphenhydramine hydrochloride | +25 mg/ml Diphenhydramine hydrochloride | +50 mg/ml Diphenhydramine hydrochloride |
|---|---|---|---|---|
| 2% E3PLV |  |  |  |  |
| Time (sec) | 94.18 | 103.57 | 69.26 | 36.66 |
|  | 95.13 | 98.80 | 74.62 | 28.04 |
|  | 78.46 | 73.91 | 44.82 | 27.69 |
|  | 35.31 | 66.68 | 72.78 | 31.45 |
|  | 34.20 | 110.71 | 94.06 | 51.68 |
|  | 59.16 | 120.28 | 111.69 | 49.31 |
|  | 90.23 | 63.11 | 90.66 | 46.82 |

TABLE 14-continued

|  | +2.5 mg/ml Diphenhydramine hydrochloride | +10 mg/ml Diphenhydramine hydrochloride | +25 mg/ml Diphenhydramine hydrochloride | +50 mg/ml Diphenhydramine hydrochloride |
|---|---|---|---|---|
|  | 68.66 | 75.98 | 99.47 | 48.80 |
|  | 73.44 | 110.20 | 93.91 | 56.00 |
|  | 81.28 | 101.49 | 93.82 | 58.04 |
| Average | 71.01 | 92.47 | 84.51 | 43.45 |
| Standard Deviation | 21.0483 | 19.5157 | 18.1931 | 10.9012 |
| 2% K3PLV |  |  |  |  |
| Time (sec) | 107.27 | 61.12 | 61.08 | 2.31 |
|  | 100.24 | 78.58 | 47.24 | 1.52 |
|  | 91.52 | 71.92 | 48.80 | 3.09 |
|  | 100.21 | 88.31 | 63.46 | 3.13 |
|  | 104.82 | 89.04 | 61.40 | 4.42 |
|  | 96.99 | 71.65 |  |  |
|  | 107.89 | 72.10 |  |  |
|  | 98.54 | 94.13 |  |  |
|  | 96.17 | 86.45 |  |  |
|  | 97.09 | 93.39 |  |  |
| Average | 100.07 | 80.67 | 56.40 | 2.89 |
| Standard Deviation | 4.9459 | 10.5960 | 6.9052 | 0.9645 |
| 0.73% A15PLV |  |  |  |  |
| Time (sec) | 152.55 | 134.11 | 162.90 | 197.75 |
|  | 127.31 | 189.53 | 148.08 | 131.55 |
|  | 166.52 | 189.12 | 164.79 | 143.45 |
|  | 116.94 | 136.95 | 167.14 | 136.01 |
|  | 143.75 | 135.59 | 155.45 | 123.54 |
|  | 161.24 | 129.34 |  |  |
|  | 132.59 | 112.10 |  |  |
|  | 167.68 | 134.75 |  |  |
|  | 166.38 | 154.90 |  |  |
|  | 134.84 | 156.70 |  |  |
| Average | 146.98 | 147.31 | 159.67 | 146.46 |
| Standard Deviation | 17.5363 | 24.1158 | 6.9941 | 26.4445 |

Example 13

The influence of the presence of Acetaminophen on the drip resistance of foams is evaluated in a series of drip-test experiments as illustrated in Table 15.

TABLE 15

|  | +2.5 mg/ml Acetaminophen | +10 mg/ml Acetaminophen | +14.28 mg/ml Acetaminophen |
|---|---|---|---|
| 2.% E3PLV |  |  |  |
| Time (sec) | 77.02 | 85.07 | 77.03 |
|  | 96.87 | 80.85 | 77.91 |
|  | 99.59 | 83.37 | 84.70 |
|  | 78.33 | 86.66 | 73.92 |
|  | 97.40 | 78.99 | 71.94 |
|  | 99.99 | 95.27 | 75.10 |
|  | 100.32 | 79.26 | 81.15 |
|  | 93.02 | 73.92 | 67.80 |
|  | 100.54 | 88.41 | 71.19 |
|  | 105.37 | 81.62 | 71.87 |
| Average | 94.85 | 83.34 | 75.26 |
| Standard Deviation | 9.0918 | 5.6170 | 4.8012 |
| 2% K3PLV |  |  |  |
| Time (sec) | 75.95 | 75.94 | 56.58 |
|  | 69.69 | 66.68 | 45.62 |
|  | 66.37 | 50.82 | 47.51 |
|  | 75.37 | 65.36 | 51.42 |
|  | 67.36 | 57.90 | 51.40 |
|  | 66.63 |  |  |
|  | 71.39 |  |  |
|  | 58.97 |  |  |
|  | 70.68 |  |  |
|  | 68.33 |  |  |
| Average | 69.07 | 63.34 | 50.51 |
| Standard Deviation | 4.6272 | 8.4893 | 3.7783 |
| 0.73% A15PLV |  |  |  |
|  | 73.36 | 76.14 | 99.47 |
|  | 48.67 | 97.22 | 82.61 |
|  | 83.25 | 88.77 | 111.15 |
|  | 91.62 | 96.10 | 99.11 |
|  | 117.40 | 121.81 | 120.80 |
| Average | 82.86 | 96.01 | 102.63 |
| Standard Deviation | 31.2035 | 33.8810 | 38.6649 |

Example 14

Aqueous solutions comprising 0.01, 7, 10, 11 and 12 percent of E3PLV respectively are prepared. 0.25 percent of dry, powdery diphenhydramine HCl is added to each of the aqueous solutions. 20 ml of the resulting solution is poured into an air-driven foam dispenser as described in Example 1. In Examples 14A and 14B the foam dispenser is compressed 5 times to eject 5 portions of foam. In all other Examples the foam dispenser is compressed twice. The tip over time is measured on a metal spoon and a plastic spoon. The tip over time is defined as the time it takes for a foam to drop off a spoon that is held upside down. The results are listed in Table 1 below.

TABLE 16

| Example No. | % E3PLV | Tip over time (foam on metal spoon) | Tip over time (foam on plastic spoon) | Foam weight (g) |
|---|---|---|---|---|
| 14A | 0.01 | Thin foam | Thin foam | 3.2 |
| 14B | 0.01 | Thin foam | Thin foam | 3.5 |
| 14C | 7 | 108 sec. | 126 sec. | 1.5 |
| 14D | 10 | Good foam, but runny | Not assessed | 3.1 |
| 14E | 10 | Good foam, but runny | Not assessed | 3.1 |
| 14F | 10 | Good foam, but runny | Not assessed | 3.0 |
| 14G | 11 | No foam | | |
| 14H | 12 | No foam | | |

Example 16

A 2 percent aqueous solution of a polymer listed in Table 18 below is filled into the air-driven foam dispenser described in Example 1. The foam quality is measured as in Example 1. The results are listed in Table 19.

TABLE 18

| | |
|---|---|
| PVP | Polyvinyl pyrrolidone of a weight average molecular weight of about 50,000 |
| PVA | Polyvinyl alcohol, weight average molecular weight 13,000-23,000, 87-89 percent hydrolyzed, commercially available from Aldrich |
| HPC | Hydroxypropyl cellulose, commercially available as Nisso-HPC, Type M, which has a viscosity of 150-400 mPa · s, measured as a 2 weight percent aqueous solution at 20° C. |

TABLE 19

| 2% PVP | | | 2% PVA | | | 2% HPC | | |
|---|---|---|---|---|---|---|---|---|
| Weight (g) | Density (g/cm$^3$) | Quality | Weight (g) | Density (g/cm$^3$) | Quality | Weight (g) | Density (g/cm$^3$) | Quality |
| 1.45 | 0.03 | 97% | 1.49 | 0.03 | 97% | 1.54 | 0.03 | 97% |
| 1.53 | 0.03 | 97% | 1.54 | 0.03 | 97% | 1.48 | 0.03 | 97% |
| 1.45 | 0.03 | 97% | 1.53 | 0.03 | 97% | 1.62 | 0.03 | 97% |
| 1.51 | 0.03 | 97% | 1.53 | 0.03 | 97% | 1.34 | 0.02 | 98% |
| 1.50 | 0.03 | 97% | 1.48 | 0.03 | 97% | 1.55 | 0.03 | 97% |
| 1.49 | 0.03 | 97% | 1.54 | 0.03 | 97% | 1.50 | 0.03 | 97% |
| 1.54 | 0.03 | 97% | 1.57 | 0.03 | 97% | 1.52 | 0.03 | 97% |
| | average density: 0.03 | average quality: 97% | | average density: 0.03 | average quality: 97% | | average density: 0.03 | average quality: 97% |
| Visual inspection of foam quality | | | Visual inspection of foam quality | | | Visual inspection of foam quality | | |
| Fizzy foam, fizz can be heard; looses its shape fast; the foam pours easily out of weight boat | | | Nice Foam, looks a bit wet in appearance; The foam holds its shape when the weight boat is tipped upside down. | | | Nice Foam, looks a bit wet in appearance. The foam holds its shape when the weight boat tipped upside down. | | |

Example 15

20 g of a 1 percent aqueous solution of E3PLV is mixed with 30 g of an oral drug composition for treating cough and cold of children. The oral drug composition is commercially available from McNeil Consumer & Specialty Pharmaceuticals under the designation Simply Stuffy. The E3PLV concentration in the resulting aqueous solution is 0.4 percent. The aqueous solution is poured into an air-driven foam dispenser as described in Example 1. In each experiment the foam dispenser is compressed twice to eject 2 portions of foam. The tip over time is measured as in Example 14.

TABLE 17

| Example No. | % E3PLV | Tip over time (foam on metal spoon) | Tip over time (foam on plastic spoon) | Foam weight (g) |
|---|---|---|---|---|
| 15A | 0.4 | 70 seconds | 79 seconds | 1.6 |
| 15B | 0.4 | 85 second | 70 second | 1.6 |

A 2 percent aqueous polymer solution is filled into the air-driven foam dispenser described in Example 1. The drip time of the foam that is ejected from the foam dispenser is measured as described in Example 10. The results are listed in Table 20.

TABLE 20

| Solution | 2% PVP | 2% PVA | 2% HPC |
|---|---|---|---|
| Drip Time (sec) | 0.43 | 13.09 | 15.78 |
| | 0.43 | 9.06 | 5.34 |
| | 0.38 | 9.15 | 7.34 |
| | 0.36 | 8.18 | 8.45 |
| | 0.33 | 11.91 | 4.90 |
| | 0.35 | 10.25 | 6.74 |
| | 0.34 | 10.16 | 6.99 |
| | 0.31 | 9.70 | 8.59 |
| | 0.30 | 11.01 | 5.43 |
| | 0.32 | 10.05 | 5.77 |
| Average | 0.36 | 10.26 | 7.53 |

A 2 percent aqueous polymer solution is filled into the air-driven foam dispenser described in Example 1. Each of the aqueous solutions additionally contains 4.17 mg/ml of diphenhydramine hydrochloride (HCl) as a drug. The drip time of the foam that is ejected from the foam dispenser is measured as described in Example 10. The results are listed in Table 21.

TABLE 21

| Solution | 2% PVP + drug | 2% PVA + drug | 2% HPC + drug |
|---|---|---|---|
| Drip Time (sec) | 0.32 | 9.96 | 7.39 |
|  | 0.45 | 8.84 | 4.09 |
|  | 0.38 | 14.45 | 3.47 |
|  | 0.41 | 8.40 | 5.51 |
|  | 0.30 | 8.09 | 4.45 |
|  | 0.26 | 7.88 | 6.83 |
|  | 0.28 | 8.77 | 4.92 |
|  | 0.27 | 8.95 | 5.05 |
|  | 0.27 | 10.28 | 5.03 |
|  | 0.29 | 12.66 | 3.74 |
| Average | 0.32 | 9.83 | 5.05 |

What is claimed is:

1. A kit for delivering pharmaceutical compositions to be ingested, wherein the kit comprises
   (a) a gas-driven foam dispenser and
   (b) a separately packed volume of a propellant-less fluid composition containing no monomeric surfactants or polymeric surfactants with a weight average molecular weight of less than 8,000 and comprising
      (i) as the only foaming agent one or more polysaccharides, having a weight average molecular weight of at least 10,000;
      (ii) a liquid diluent, and
      (iii) an active ingredient for oral medicinal treatment or hygiene,
   wherein the viscosity of the fluid composition is from 2 to 50 mPa·s at 20° C.

2. The kit of claim 1 wherein the polysaccharide is a cellulose ether.

3. The kit of claim 1 wherein the cellulose ether is a $C_1$-$C_3$-alkyl cellulose, $C_1$-$C_3$-alkyl hydroxy-$C_{1-3}$-alkyl cellulose, hydroxy-$C_{1-3}$-alkyl cellulose or a mixed hydroxy-$C_1$-$C_3$-alkyl cellulose having a weight average molecular weight of from 12,000 to 100,000.

4. The kit of claim 1 comprising an air-driven foam dispenser (a) and a propellant-less fluid composition (b).

5. The kit of claim 1 wherein the polysaccharide is a hydroxypropyl methylcellulose or a methylcellulose.

6. The kit of claim 1 wherein the polysaccharide is a hydroxypropyl methylcellulose or methylcellulose having a weight average molecular weight of from 12,000 to 100,000.

7. The kit of claim 1 wherein the propellant-less fluid composition (b) comprises from 0.1 to 5 percent of one or more polysaccharides as the only foaming agent, based on the total weight of the fluid composition.

8. The kit of claim 1 wherein the propellant-less fluid composition (b) comprises from 0.005 to 5 percent of an active ingredient, based on the total weight of the fluid composition.

* * * * *